United States Patent [19]

Whiteside et al.

[11] Patent Number: 5,019,104
[45] Date of Patent: May 28, 1991

[54] PATELLAR PROSTHESIS AND METHOD OF MAKING THE SAME

[75] Inventors: Leo A. Whiteside, St. Louis, Mo.; Bradley J. Coates, Cordova, Tenn.

[73] Assignee: Dow Corning Wright Corporation, Arlington, Tenn.

[21] Appl. No.: 466,093

[22] Filed: Jan. 16, 1990

[51] Int. Cl.$^5$ ................................................ A61F 2/38
[52] U.S. Cl. ...................................... 623/20; 623/901; 264/274
[58] Field of Search ...................... 623/20, 18, 16, 901

[56] References Cited

U.S. PATENT DOCUMENTS

| | | | |
|---|---|---|---|
| 4,094,017 | 6/1978 | Matthew et al. | 623/20 |
| 4,205,400 | 6/1980 | Shen et al. | 623/20 X |
| 4,240,162 | 12/1980 | Devas | 623/20 |
| 4,479,274 | 10/1984 | Bolesky et al. | 623/18 X |

FOREIGN PATENT DOCUMENTS 3332354 3/1985 Fed. Rep. of Germany ........ 623/20

OTHER PUBLICATIONS

Howmedica, Inc., Orthopedics Division, 359 Veterans Blvd. Rutherford, NJ 07070 No. H2030, dated 3/83 "The PCA Revision Total Knee System" at page 4.

Dow Corning Wright Corporation, 5677 Airline Rd., Arlington, TN 38002 No. 322-688T (1988) "Whiteside Ortholoc II Patella Implants".

*Primary Examiner*—Ronald Frinks
*Attorney, Agent, or Firm*—Allan O. Maki; John L. Chiatalas

[57] ABSTRACT

A composite metal/plastic patellar prosthesis for implantation in the human body to replace the articulating surface of the patella is provided. The prosthesis includes a polymeric articulating surface portion and a metal backing having an anterior surface adapted to be attached to the posterior surface of a resected patella, and a dome or conically shaped posterior surface to which the polymeric articulating surface portion is heat and pressure molded. The metal backing portion has at least one aperture extending therethrough which has a greater cross-sectional area on the anterior side than on the posterior side into which an anchoring peg integral with the antrior surface of the polymeric articulating surface portion is molded. The metal and plastic components of the composite are coextensive in size and shape.

4 Claims, 1 Drawing Sheet

PATELLAR PROSTHESIS AND METHOD OF MAKING THE SAME

BACKGROUND OF THE INVENTION

The present invention relates to an improved patellar prosthesis and method of making the same.

Various prosthetic devices for replacement of the articulating surface of the patella or knee cap have been designed for implantation in cases where replacement of the natural articulating surface of the patella is indicated. Generally, the posterior surface of the patella is resected and replaced by an artificial articulating surface.

Various patellar prostheses are known in the art and available commercially to surgeons. Examples of such are the designs shown in U.S. Pat. No. 4,240,162 issued to Devas on Dec. 23, 1980 in which a two-part snapped-together design is disclosed. Commercially available implants are shown, for example, in Publication No. 322-688T of Dow Corning Wright Corporation, 5677 Airline Road. Arlington. TN 38002 entitled "Whiteside Ortholoc II Patella Implants". Similar designs having a metal backing within a polymeric surface portion are shown, for example, in a publication by Howmedica, Inc., Orthopedics Division, 359 Veterans Boulevard, Rutherford, NJ 07070 identified as No. H2050, dated 3/83, entitled "The PCA Revision Total Knee System" at page 4. Such prostheses have been known to fail by virtue of separation of the polymeric articulating surface from the metal backing.

In light of these various designs, a need has existed for an improved patellar prosthesis having resistance to shear forces experienced during articulation of the patellar implant against an articulating surface of a femoral prosthesis. The present invention provides such increased resistance by a design in which shear forces imposed against the side of the patellar implant are, in part, converted to compression forces. The invention further provides a means and method of molding the polymeric articulating surface onto the metal backing in such fashion as to improve the mechanical locking, and thus resistance to wear, between the components of the prosthesis.

Briefly summarized, the present invention provides a composite patellar prosthesis for implantation in the human body to replace the articulating surface of the patella which includes a polymeric articulating surface portion, and a dome shaped metal backing which has an anterior surface adapted to be attached to the posterior surface of a resected patella, preferably by means of integral attachment pegs. The dome shaped, or otherwise centrally elevated posterior surface is adapted to engage the polymeric articulating surface portion which is molded under heat and pressure to conform to it. The metal backing portion is provided with at least one, and preferably several apertures extending therethrough which have a greater cross-sectional area on the anterior side than on the posterior side. These apertures are each adapted to fixedly receive an anchoring peg integral with the anterior surface of the polymeric articulating surface portion, the pegs being formed under heat and pressure to precisely fill the apertures. It is also preferred that the anterior surface of the polymeric articulating surface portion is coextensive in size and shape with the metal backing portion is molded to conform to the contour thereof. The articulating surface portion has a generally convex posterior articulating surface. The apertures through the metal backing are greater in area on the anterior side than on the posterior side so that the pegs firmly lock the two parts of the composite together. The anterior side may, for example, be counterbored or the apertures may be tapered or flared so as to be of greater size on the anterior side.

DRAWINGS

The invention will be further explained with reference to the accompanying drawings wherein:

FIG. 1 is a perspective view of a patellar prosthesis of the present invention, and, FIG. 2 is a cross-sectional view of such a prosthesis.

DETAILED DESCRIPTION

Figure 1:
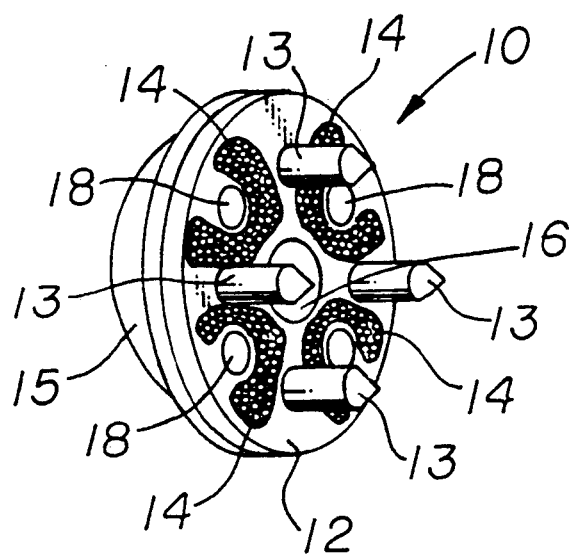

Referring more specifically to the drawings, patellar prosthesis 10 is formed from a rigid, preferably metallic backing portion 12, provided on its anterior surface with integrally formed securing pegs 13 which are provided to secure the prosthesis to the posterior side of a resected patella. In accordance with conventional practice, the anterior surface of metallic attachment portion 12 can be provided with a porous layer such as sintered metal microbeads 14 to allow for tissue ingrowth.

Secured to the posterior side of metallic supporting layer 12 is a polymeric surface layer 15 preferably formed from a thermoplastic material such as ultra high molecular weight polyethylene. Other biologically acceptable moldable materials such as polypropylene or the like can be substituted in articulating surface 15. Polymeric articulating surface portion 15 is preferably formed so that it is the same size and shape as the metal backing element 12, and the anterior side of the articulating surface member is pressure molded so that it flows and conforms to the posterior surface of metal backing element 12.

The polymeric surface portion is affixed to the metal backing portion by means of one or more integral pegs 16 which are molded by heat and pressure into an apertures extending through metal backing member 12. The apertures are configured so that the anterior side is larger than the posterior side, for example by means of a counter-bored portion 17 on the anterior side, or by means of slightly tapered or anteriorly flared openings. The preferred embodiment, shown in the drawings, utilizes one central peg 16 along with four smaller pegs 18 all of which are heat and pressure molded into the apertures to provide a secure attachment of the backing member to the wear surface.

Figure 2:
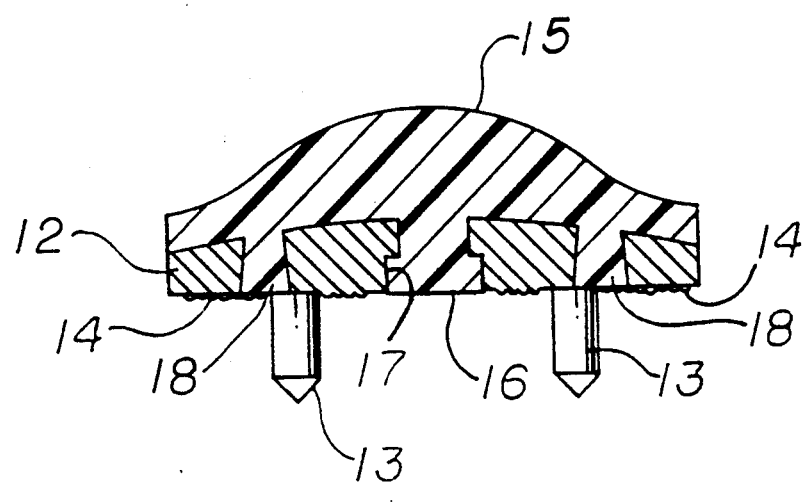

Also as seen best in FIG. 2, the central portion of the metal backing portion 12 is centrally thickened into a domed shape. This configuration has been found to be superior to prior art devices in which flat abutting surfaces were employed. Such flat surfaces may be subjected to shearing forces as the prosthesis wears, whereas the slightly dome shaped configuration of the present prosthesis causes a vector of those shearing forces to be converted into compression forces which have been discovered to be more resistant to failure at the junction between the parts of the composite prosthesis.

The prosthesis of the present invention is formed by providing a plastic blank of the articulating surface which is provided with a central peg having a height slightly greater than the thickness of the metal backing member 12. When molded under heat and pressure the anterior surface of the plastic member is forced to assume the contour of the metal backing member and the central, peg flows into the undercut portion 17 of the central aperture. The apertures spaced around the central aperture, however, are of a smaller diameter and it has been found that the plastic material of the articulating surface 15 will flow into such apertures under heat and pressure, to fill the apertures as shown in FIG. 2. This method of construction obviates the need for formation of additional pegs on the anterior surface of the articulating portion blank. If desired, however, additional pegs could be employed, particularly if it is desired to use somewhat larger diameter apertures than indicated in FIG. 1.

The prosthesis of the present invention is implanted in accordance with usual surgical procedures followed for implantation of patellar prostheses. Such procedures, therefore, will not be elaborated on in the present disclosure.

While the foregoing specification give a detailed description of specific embodiments of the invention for the purpose of illustration, it will be understood that many of the details given may be varied considerably by those skilled in the art without departing from the spirit and the scope of the invention.

That what is claimed is:

1. A patellar prosthesis for implantation in the human body to replace the articulating surface of the patella comprising:
    a polymeric articulating surface portion, and,
    a metal backing having an anterior surface adapted to be attached to the posterior surface of a resected patella, and a posterior surface adapted to engage the polymeric articulating surface portion, said metal backing portion having a central portion that is thicker than the outer edges thereof, said central portion being elevated on the posterior surface of said backing and having at least one aperture extending therethrough which has a greater cross-sectional area on the anterior side than on the posterior side thereof, adapted to fixedly receive an anchoring peg integral with the anterior surface of the polymeric articulating surface portion, said anterior surface of said articulating surface portion being coextensive in size and shape with said metal backing portion and being molded to conform to the contour thereof, said articulating surface portion have a generally convex posterior articulating surface, said anchoring peg being molded into said aperture and filling substantially the entire volume thereof.

2. A prosthesis according to claim 1 wherein said metal backing also contains a plurality of small apertures each of which is of increasing diameter in the posterior to anterior direction.

3. A method of making a patellar prosthesis for implantation in the human body to replace the articulating surface of the patella comprising:
    providing a polymeric articulating surface portion blank, and,
    a metal backing portion which has an anterior surface adapted to be attached to the posterior surface of a resected patella, and a dome shaped posterior surface adapted to engage the polymeric articulating surface portion, said metal backing portion having at least one aperture extending therethrough which has a greater cross-sectional area on the anterior side than on the posterior side thereof, adapted to fixedly receive an anchoring peg integral with the anterior surface of the polymeric articulating surface portion, said anterior surface of said articulating surface portion blank being coextensive in size and shape with said metal backing portion and capable of being molded to conform to the contour thereof, said articulating surface portion having a generally convex posterior articulating surface.
    molding said polymeric surface portion blank onto the posterior side of said metal backing under heat and pressure so that said anchoring peg is molded into said aperture and fills substantially the entire volume thereof.

4. A method according to claim 3 wherein said metal backing contains small diameter apertures therethrough which are of increasing diameter in the posterior to anterior direction, and said apertures become filled with said polymeric material under application of such heat and pressure.

* * * * *